United States Patent [19]
Nagai et al.

[11] Patent Number: 5,186,810
[45] Date of Patent: Feb. 16, 1993

[54] OXYGEN SENSOR

[75] Inventors: Takeshi Nagai, Nara; Kunihiro Tsuruda, Kashihara, both of Japan

[73] Assignee: Matsushita Electric Industrial Co., Ltd., Osaka, Japan

[21] Appl. No.: 651,853

[22] Filed: Feb. 7, 1991

[30] Foreign Application Priority Data

Feb. 13, 1990 [JP] Japan .................................. 2-32024

[51] Int. Cl.$^5$ .......................................... G01N 27/26
[52] U.S. Cl. ................................ 204/425; 204/410; 204/406; 204/426
[58] Field of Search .......... 204/410, 400, 406, 153.18, 204/426, 425, 424

[56] References Cited

U.S. PATENT DOCUMENTS

| | | | |
|---|---|---|---|
| 3,942,104 | 3/1976 | Byrue | 204/400 |
| 4,668,374 | 5/1987 | Bhagat et al. | 204/412 |
| 4,670,128 | 6/1987 | Mase et al. | 204/426 |
| 4,728,411 | 3/1988 | Mase et al. | 204/426 |
| 4,808,293 | 2/1989 | Fukuda et al. | 204/410 |
| 4,824,548 | 4/1989 | Iino et al. | 204/410 |
| 4,927,517 | 5/1990 | Mizutani et al. | 204/425 |

FOREIGN PATENT DOCUMENTS

| | | |
|---|---|---|
| 526247 | 12/1982 | Australia . |
| 580726 | 1/1989 | Australia . |
| 0104636 | 4/1984 | European Pat. Off. . |
| 0166530 | 1/1986 | European Pat. Off. . |
| 60-128058 | 10/1985 | Japan . |
| 2-12049 | 1/1990 | Japan . |
| 2-34605 | 9/1990 | Japan . |

*Primary Examiner*—John Niebling
*Assistant Examiner*—Bell Bruce F.
*Attorney, Agent, or Firm*—Lowe, Price, Leblanc & Becker

[57] ABSTRACT

An oxygen ion conductive solid-electrolyte plate (1) has first and second opposite surfaces. A plurality of negative electrodes (21b, 22b) and positive electrodes (21a, 22a) are formed on the first and second surfaces of the solid-electrolyte plate (1), respectively, and each of the plurality of negative electrodes (21b, 22b) is opposed to each of the plurality of positive electrodes (21a, 22a). A spacer (5 or 7) is hermetically secured to the first surface of the electrolyte plate (1) and at the same time surrounds each of the plurality of negative electrodes (21b, 22b). A sealing plate (3) is also hermetically secured to the spacer (5 or 7). A plurality of closed spaces (61, 62) are thus defined as spaces surrounded by the solid-electrolyte plate (1), spacer (5 or 7) and sealing plate (3). A plurality of windows (41, 42) are provided in the sealing plate. Each of the plurality of closed spaces (61, 62) embraces one negative electrode of the plurality of negative electrodes (21b, 22b) and one window of the plurality of windows (41, 42). Each of the plurality of closed spaces (61, 62) communicates with the external space through one of the plurality of windows (41, 42). Each of the plurality of windows (41, 42) allows oxygen molecules to diffusely flow from the environment into each of the plurality of closed spaces (61, 62) through each of the plurality of windows (41, 42).

4 Claims, 10 Drawing Sheets

OXYGEN SENSOR

BACKGROUND OF THE INVENTION

1. Field of the Invention

This invention relates to an oxygen sensor for detecting oxygen concentration.

2. Description of the Prior Art

Various types of oxygen sensors are hitherto known. Japanese Utility Model Publication 2-34605 discloses an oxygen sensor of a limiting current type having two internal chambers. The two chambers are each constituted of an oxygen ion conductive solid-electrolyte plate, electrodes formed on both surfaces of the solid electrolyte plate, a support, and a sealing layer that hermetically secure the solid electrolyte plate and the support at their ends. The first and second chambers holds the same support in common. The first chamber communicates with its surrounding space through a first gas diffusion controlling small orifice. The second chamber communicates with the first chamber through a second gas diffusion controlling small orifice provided on the common support. When the first small orifice has been closed up with dust, this sensor can detect an increase in the diffusion resistance at the small orifice.

Japanese Laid-open Patent Application No. 2-12049 disclosed a similar structure. When an electrode has been deteriorated because of adhesion of dust such as an oxide, this sensor can detect a decrease in limiting currents.

Japanese Laid-open Patent Application No. 60-218058 discloses a method for the self-examination by a sensor, performed when limiting currents have decreased as a result of the deterioration of an oxygen sensor. This sensor has one internal chamber. This chamber is constituted of an oxygen ion conductive solid-electrolyte plate, electrodes formed on both surfaces of the solid electrolyte plate, a support, and a sealing layer that hermetically secure the solid electrolyte plate and the support at their ends. According to this method, two different voltages are alternately applied between the electrodes. The deterioration of the sensor is detected according to changes in correlation between two limiting currents.

SUMMARY OF THE INVENTION

A first object of the present invention is to provide an oxygen sensor capable of detecting a change in diffusion resistance when a small orifice has been closed with dust or fine cracks have been produced in a sealing layer.

A second object of the present invention is to provide an oxygen sensor capable of detecting an decrease of limiting currents when an electrode has been deteriorated because of adhesion of dust such as an oxide.

In the oxygen sensor of the present invention, an oxygen ion conductive solid-electrolyte plate has first and second opposite surfaces. A plurality of negative electrodes and positive electrodes are formed on the first and second surfaces of the solid-electrolyte plate, respectively, and each of the plurality of negative electrodes is opposed to each of the plurality of positive electrodes. A spacer is hermetically secured to the first surface of the electrolyte plate and at the same time surrounds each of the plurality of negative electrodes. A sealing plate is also hermetically secured to the spacer. A plurality of closed spaces are thus defined as spaces surrounded by the solid-electrolyte plate, spacer and sealing plate. A plurality of windows are provided in the sealing plate. Each of the plurality of closed spaces embraces one negative electrode of the plurality of negative electrodes and one window of the plurality of windows. Each of the plurality of closed spaces communicates with the external space (or the environment) through one of the plurality of windows. Each of the plurality of windows allows oxygen molecules to diffusely flow from the environment into each of the plurality of closed spaces through each of the plurality of windows.

DESCRIPTION OF THE PREFERRED EMBODIMENTS

Figure 1:
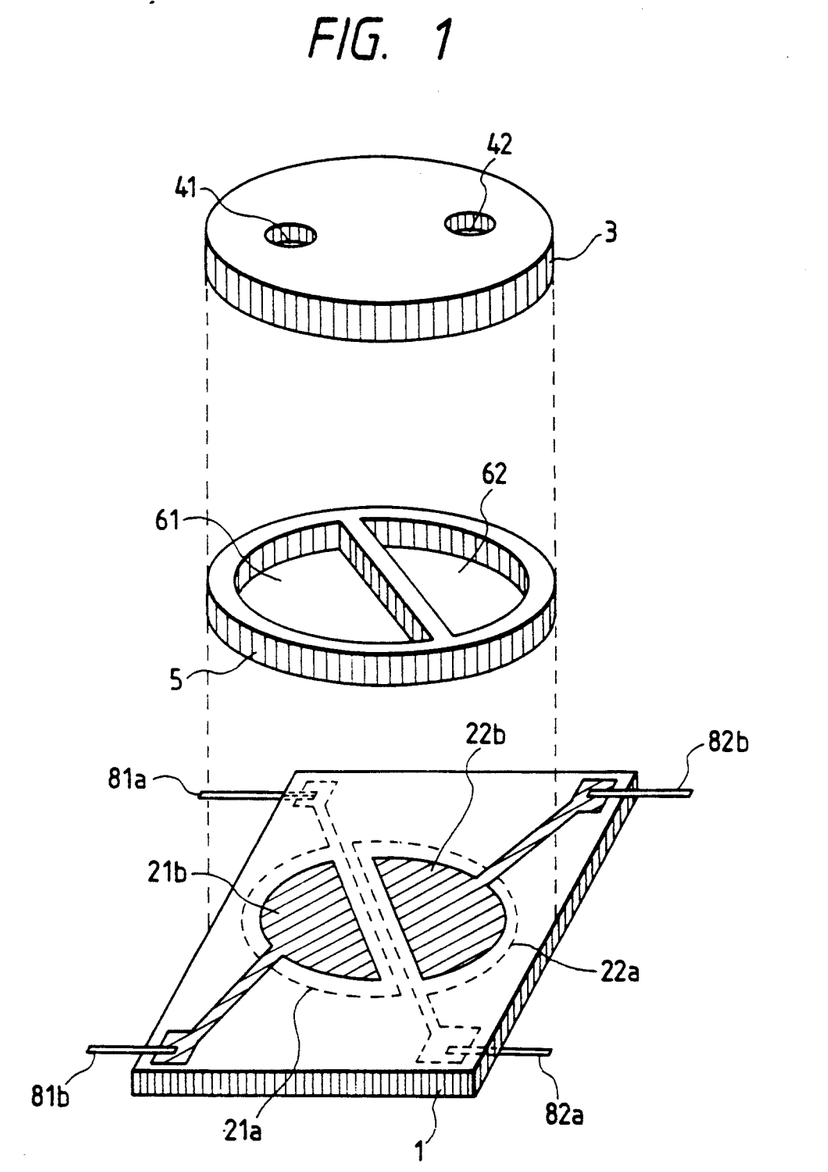
FIG. 1 is a perspective exploded view of an oxygen sensor according to an embodiment of the present invention.

FIG. 1 shows a perspective exploded view of an oxygen sensor according to an embodiment of the present invention. This sensor is comprised of an oxygen ion conductive solid-electrolyte plate 1 having two positive electrodes 21a and 22a and two negative electrodes 21b and 22b, a sealing plate 3 having two windows 41 and 42, and a spacer 5.

Figure 4:
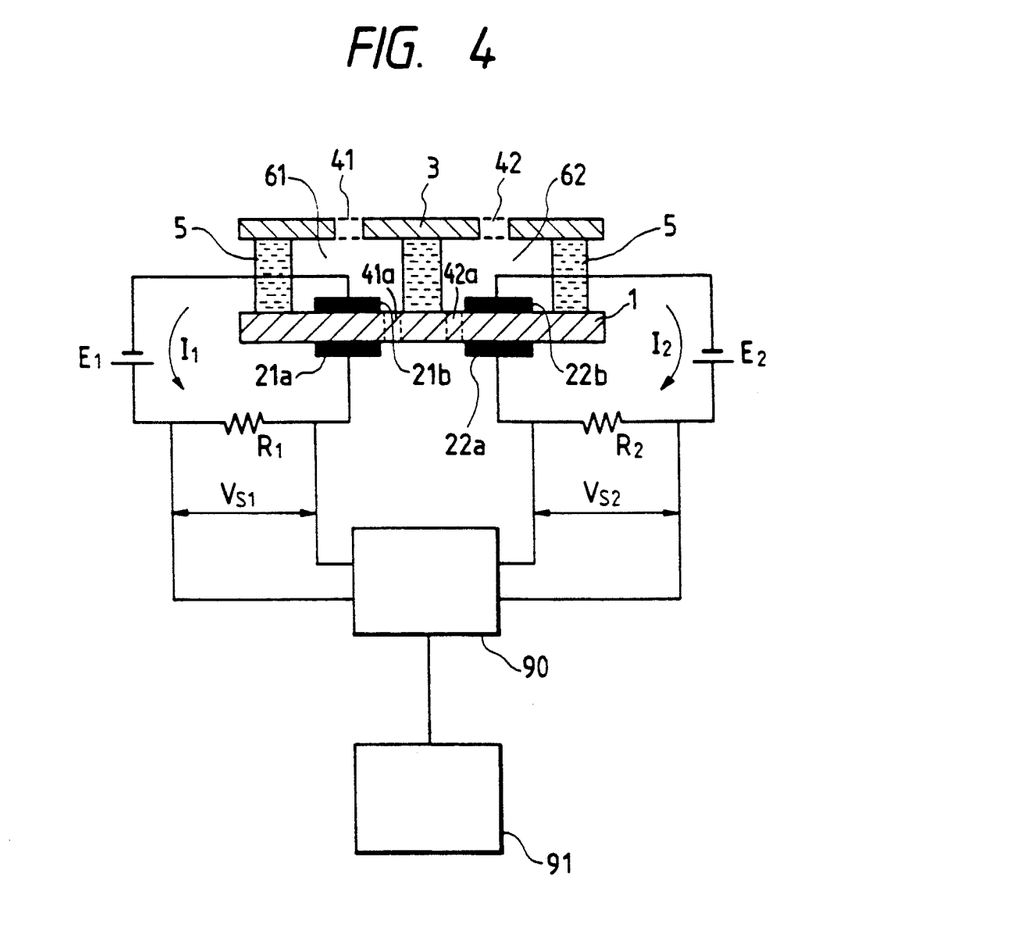
FIG. 4 illustrates a deterioration detecting means.

The two positive electrodes 21a and 22a and the two negative electrodes 21b and 22b are formed in close adhesion to the opposite surfaces of the solid-electrolyte plate 1, respectively. The positive electrodes 21a and 22a are opposed to the negative electrodes 21b and 22b, respectively. The solid-electrolyte plate 1 is hermetically secured at its periphery to the sealing plate 3 through means of the spacer 5. The spacer 5 separately surrounds the negative electrodes 21b and 22b. Two closed spaces 61 and 62 are defined as spaces surrounded by the solid-electrolyte plate 1, sealing plate 3 and spacer 5. The two windows 41 and 42 are provided in the sealing plate 3 in such a way that the two closed spaces 61 and 62 may communicate with the external space through the two windows 41 and 42, respectively. Thus, a first sensor element is comprised of the positive electrode 21a, the negative electrode 21b, the window 41 and the closed space 61. A second sensor element is comprised of the positive electrode 22a, the negative electrode 22b, the window 42 and the closed space 62. The same applies also to an instance in which the two windows 41 and 42 provided in the sealing plate 3 are replaced with two windows 41a and 42a provided in the solid-electrolyte plate 1 as shown in FIG. 4. As is clear from the above description, the oxygen sensor of the present invention has the structure that a plurality of sensor elements are integrated on one solid-electrolyte plate 1.

Figure 2:
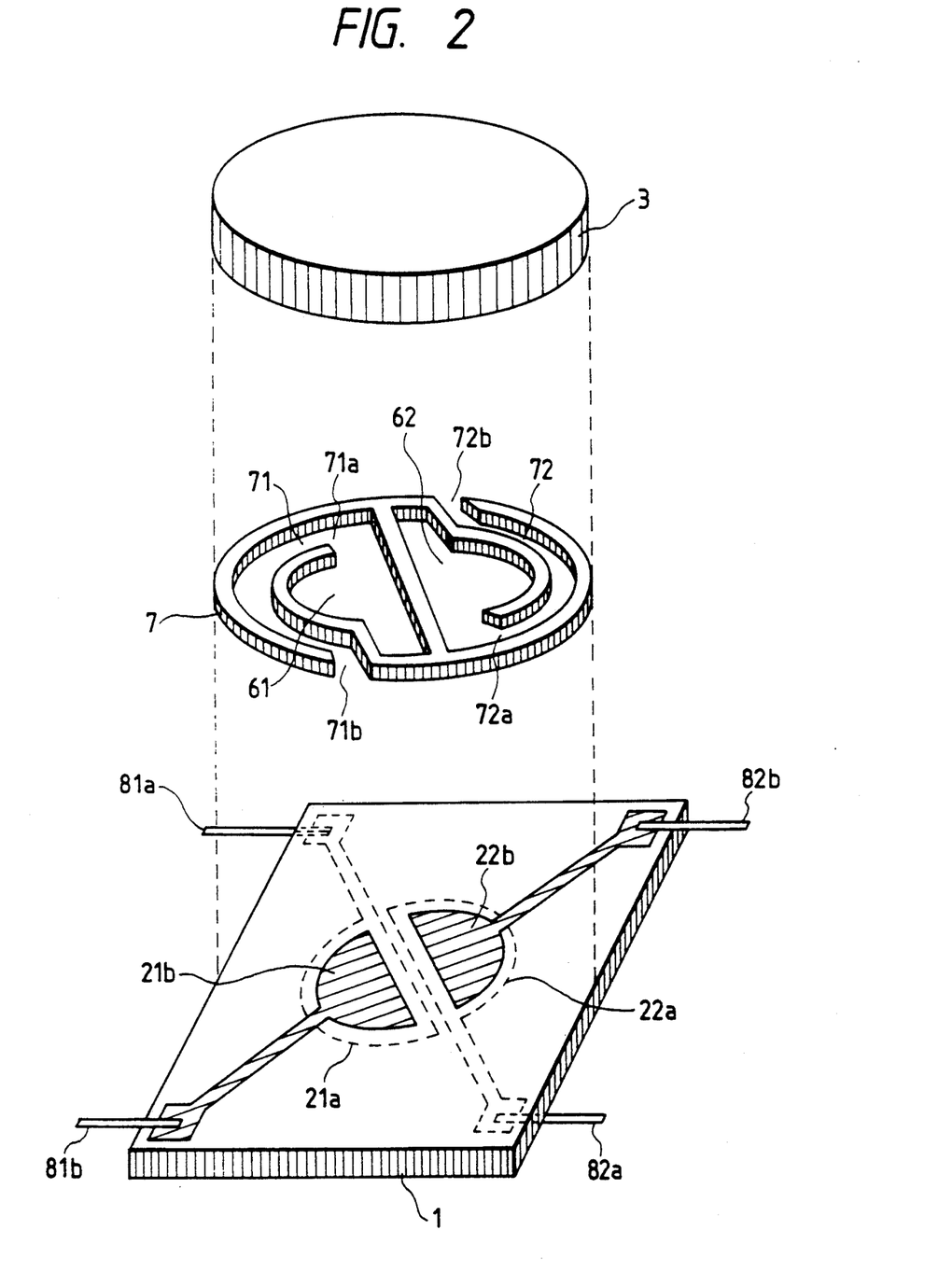
FIG. 2 is a perspective exploded view of an oxygen sensor according to another embodiment of the present invention.

FIG. 2 shows a perspective exploded view of an oxygen sensor according to another embodiment of the present invention. In this sensor, a sealing plate 3 with dense structure not provided with the two windows 41 and 42 as shown in FIG. 1. is used. A spacer 7 with the structure capable of communicating with the external space (i.e., a communicating spacer 7) is also used in place of the spacer 5 with dense structure as shown in FIG. 1. The communicating spacer 7 has two diffusion paths 71 and 72 of spiral forms having open ends 71$b$ and 72$b$ and inner ends 71$a$ and 72$a$, respectively. The two spiral diffusion paths 71 and 72 corresponds to the two windows 41 and 42 shown in FIG. 1. The solid-electrolyte plate 1 is hermetically secured to the sealing plate 3 with dense structure. The communicating spacer 7 separately surrounds negative electrodes 21$b$ and 22$b$. Two closed spaces 61 and 62 are defined in the same way as shown in FIG. 1. As a result, first and second sensor elements are defined also in the same way as shown in FIG. 1.

The oxygen sensor shown in FIG. 2 is more advantageous than the oxygen sensor shown in FIG. 1, in respect of the following: In the latter, the windows 41 and 42 with fine size of several tens microns in diameter and 0.5 to 2 mm in length must be formed in the sealing plate 3 made of ceramics such as mullite. In the former, however, it is not necessary to form the window-like diffusion path with such a fine size in the ceramic plate, and is enough to form the spiral diffusion paths 71 and 72 with a larger size of 0.4 to 0.8 mm in width, several tens microns in height and about 10 to 20 mm in length, so that the diffusion path can be readily formed using a thick glass film. Techniques therefor are detailed in U.S. Pat. No. 4,808,293.

Since the oxygen sensor shown in FIG. 1 and the oxygen sensor shown in FIG. 2 can operate similarly, the following is decribed with reference to the oxygen sensor shown in FIG. 1.

Typical materials and dimensions of its components are as shown below: $Zr_2O_3$ ceramic of 10 mm square and 0.5 to 1 mm thick, doped with 8 mol % of $Y_2O_3$, is used as the solid-electrolyte plate 1. Fired thick Pt films are used as the positive electrodes 21$a$ and 22$a$ and negative electrodes 21$b$ and 22$b$. The Pt thick film electrodes may each be typically 5 to 15 $\mu$m in thickness. A backed thick glass film is used as the spacer 5. The thick glass film may be typically 20 to 40 $\mu$m in thickness. A ceramic material such as forsterite or $Zr_2O_3$ of 10 mm in diameter and 0.5 to 1 mm in thickness is used as the sealing plate 3. The windows 41 and 42 may each be 20 to 40 $\mu$m in diameter and 0.5 to 1 mm in length.

When the sensor is operated, it is kept at a high temperature of from 400° to 550° C., and a DC power source is connected to the positive electrodes 21$a$ and 22$a$ and negative electrodes 21$b$ and 22$b$. Oxygen molecules pass through the windows 41 and 42 by diffusion and are thus transported from the external space the closed spaces 61 and 62. The oxygen molecules thus transported are all ionized on the negative electrodes 21$b$ and 22$b$, and the oxygen ions pass from the negative electrodes 21$b$ and 22$b$ through the solid-electrolyte plate 1 to reach the positive electrodes 21$a$ and 22$a$. The oxygen ions turn into oxygen molecules on the positive electrodes 21$a$ and 22$a$ and then are emitted to the outer space. In this course of operation, the solid-electrolyte plate 1 has the ability to emit the oxygen molecules in a quantity more than the quantity of those transported from the external space to the closed spaces 61 and 62. On the other hand, the quantity of the oxygen molecules transported thereto depends on the diffusion resistance of the windows 41 and 42 and the concentration of oxygen in the external space. As a result, since the solid-electrolyte plate 1 emits all the oxygen molecules transported, the oxygen ionic current (limiting current) present at that time corresponds with the oxygen concentration so long as the diffusion resistance is constant.

Figure 3:
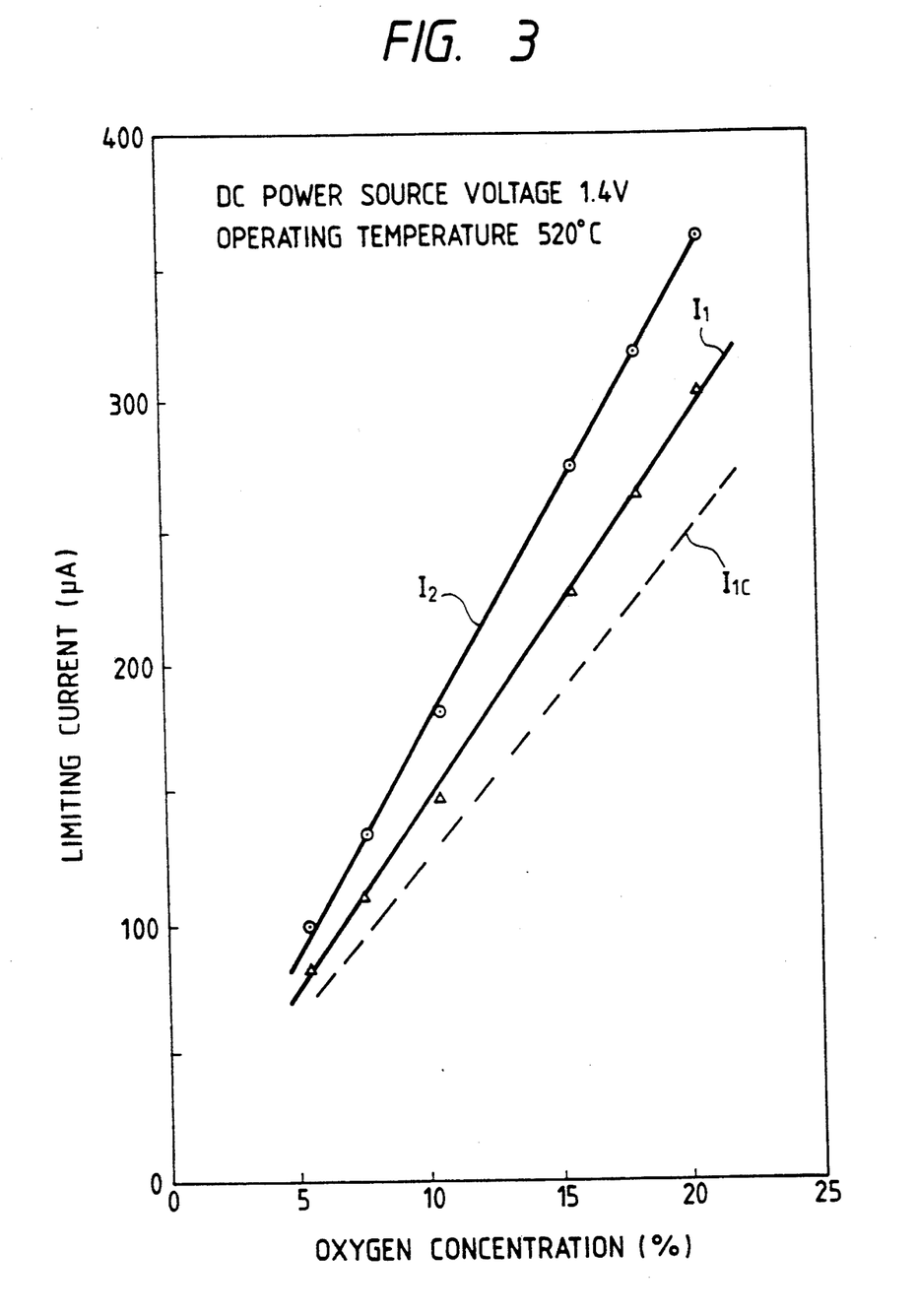
FIG. 3 shows limiting current-oxygen concentration characteristics.

Since the oxygen sensor shown in FIG. 1 has the structure that two sensor elements are integrated on one solid-electrolyte plate 1, two limiting currents can be obtained there. FIG. 3 shows a typical oxygen concentration dependence of the two limiting currents. Solid lines $I_1$ and $I_2$ correspond with the characteristics of the first and second sensor elements, respectively. The limiting currents can be represented by the following expressions:

$$I_1 = (K_1 T_1^n / R_{d1}) \ln[1/(1-x)]$$

$$I_2 = (K_2 T_2^n / R_{d2}) \ln[1/(1-x)]$$

wherein $T_1$ and $R_{d1}$, and $T_2$ and $R_{d2}$ represent operating temperature and diffusion resistance of the first and second sensor elements, respectively; x represents oxygen concentration in the external space; $K_1$ and $K_2$ represent constants and $K_1 = K_2$ when $T_1 = T_2$; and n represents a constant of about 0.75. The operating temperature is produced by the electrical heating of a coil heater comprising a metal wire, provided in the vicinity of the sensors, or a filmy heater formed on the sealing plate 3. Since the first and second sensor elements are integrated on one solid-electrolyte plate 1 in very close arrangement, the operating temperatures $T_1$ and $T_2$ are substantially equal. Hence, in the oxygen sensor of the present invention, the relation of substantially $K_1 = K_2$ can be formed. In this instance, the difference between diffusion resistances $R_{d1}$ and $R_{d2}$ results from the difference of the shapes of the windows 41 and 42, respectively, and consequently results in the difference between $I_1$ and $I_2$.

Once the window 41 has been partly closed up with dust or the like such as fine oxide particles, it becomes hard for the oxygen molecules in the external space to be diffused into the closed space 61, and hence the diffusion resistance $R_{d1}$ increases. As a result, $I_1$ decreases in proportion to the reciprocal of $R_{d1}$. When in an experiment the window 41 was partly closed up with a metal thin wire of about 10 $\mu$m in diameter, the limiting current of the first sensor element decreased from the initial current $I_1$ to a lower current $I_{1c}$ as shown in FIG. 3 by a dotted line $I_{1c}$. On the other hand, since the window 42 is not closed up, the limiting current of the second sensor element remains unchanged from the initial limiting current $I_2$. Since consequently the mutual relation between $I_1$ and $I_2$ changes, this changes may be detected to detect the close-up of the window 41. The same results can be obtained also when the window 42 is partly closed up and the window 41 is not closed up. If the spacer 5 has been finely cracked at the outer periphery of the closed space 61, the oxygen molecules in the outer space may diffuse into the closed space 61 through not only the window 41 but also the cracked portion, so that the effective diffusion resistance $R_{d1}$ decreases. In such an instance, it is difficult to make confirmation by an experimental route. It, however, is apparent that the influence of dust or the like or fine cracks can be detected based on the changes in the mutual relation between $I_1$ and $I_2$.

When the above changes in the mutual relation are detected, it is preferred to detect changes in a ratio of $I_1/I_2$. The ratio $I_1/I_2$ can be represented by the following expression under conditions of approximately $T_1 = T_2$:

$$I_1/I_2 = R_{d2}/R_{d1}$$

Since the ratio $I_1/I_2$ does not depend on the oxygen concentration, the changes of $R_{d1}$ or $R_{d2}$ can be readily detected even under various oxygen concentrations. As shown in FIG. 4, a means for detecting the ratio $I_1/I_2$ should preferably be provided with DC power source means $E_1$ and $E_2$, resistance means $R_1$ and $R_2$, a voltage ratio detecting means 90 and a comparison means 91. The DC power source means $E_1$ and $E_2$ and the resistance means $R_1$ and $R_2$ are connected in series to the first and second sensor elements, respectively. When the two limiting currents $I_1$ and $I_2$ flow in the resistance means $R_1$ and $R_2$, respectively, two signal voltages $V_{s1}$ and $V_{s2}$ are obtained. The two signal voltages $V_{s1}$ and $V_{s2}$ are separately inputted to the voltage ratio detecting means 90. Finally, the output of the voltage ratio detecting means 90 is inputted to the comparison means 91.

Figure 5:
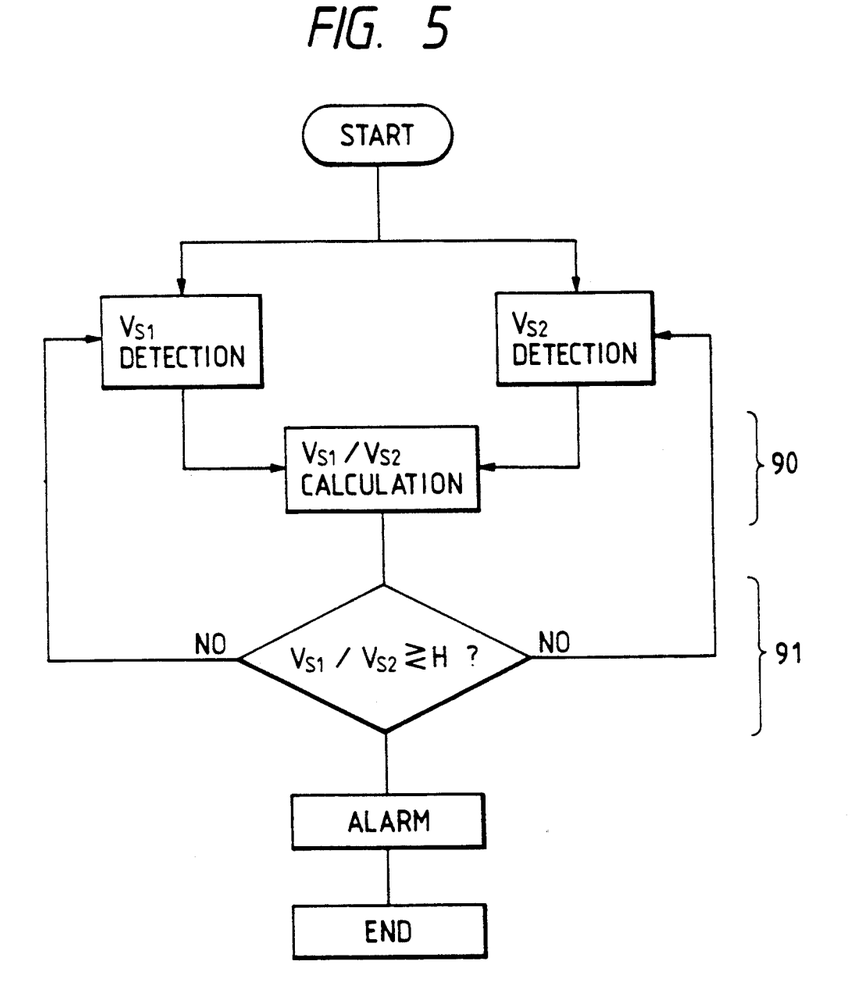
FIG. 5 is a flow chart to show a deterioration detecting process.

FIG. 5 shows a flow chart of the operation in this detecting means. First, the signal voltages $V_{s1}$ and $V_{s2}$ are measured. The measured values are inputted to the voltage ratio detecting means 90, where a ratio $V_{s1}/V_{s2}$ is detected. Next, the ratio $V_{s1}/V_{s2}$ is inputted to the comparison means 91, and compared with a given value H. An alarm is given when the ratio $V_{s1}/V_{s2}$ is larger or smaller than the given value H. On the other hand, the above process is continued when the ratio $V_{s1}/V_{s2}$ is substantially equal to the given value H.

This detecting means, however, has the disadvantage that the $R_{d1}$ and $R_{d2}$ may scatter for each sample and hence the ratio $V_{s1}/V_{s2}$ may also differ for each sample. The diffusion resistances $R_{d1}$ and $R_{d2}$ may scatter by several tens %. Hence, the ratio $V_{s1}/V_{s2}$ may also scatter to substantially the same extent. This indicates that the given value H must be individually determined for each of a number of sensors when oxygen sensors of this type have been manufactured. Such a process, which requires complicated operations and much time, is not preferable. In order to eliminate such a disadvantage, resistances $R_1$ and $R_2$ should preferably be controlled so as to give $V_{s1} = V_{s2} = V_s$ (the given value). The given value can thereby be H = 1 even if there is a scatter of the diffusion resistances $R_{d1}$ and $R_{d2}$. This indicates that it is unnecessary to determine the given value H for each sample. The resistances $R_1$ and $R_2$ can be readily controlled using a variable resistor.

Figure 6:
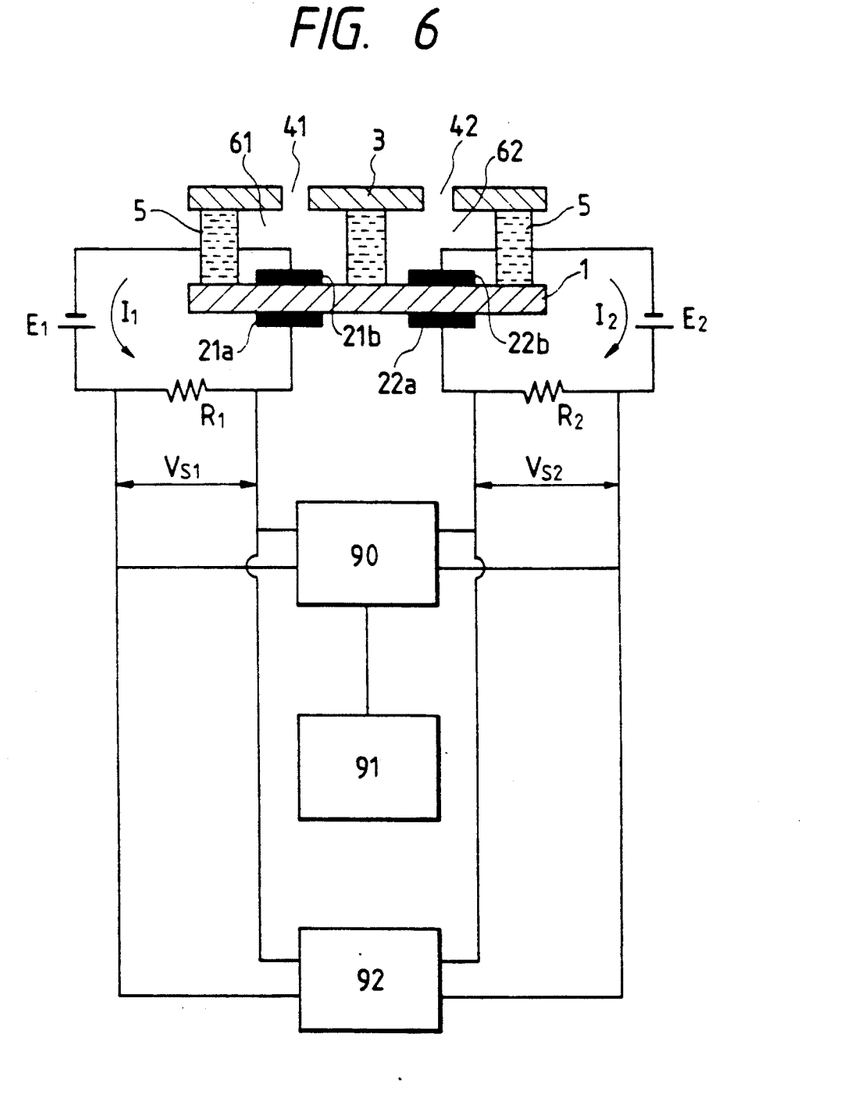
FIG. 6 illustrates an oxygen concentration detecting means provided with a deterioration detecting means.

As shown in FIG. 6, it is more preferable to add a total-voltage detecting means 92 to the construction shown in FIG. 5. Of course, the respective signal voltages $V_{s1}$ ($= V_s$) and $V_{s2}$ ($= V_s$) are signals corresponding with the oxygen concentration. Hence, total signal voltage $V_{s1} + V_{s2}$ ($= 2V_s$) is also a signal corresponding with the oxygen concentration. However, the sensitivity of the total signal voltage $2V_s$ is twice greater than the sensitivity of the single signal voltage $V_s$.

The detection of deterioration of the negative electrodes 21b and 22b will be described below.

Figure 7:
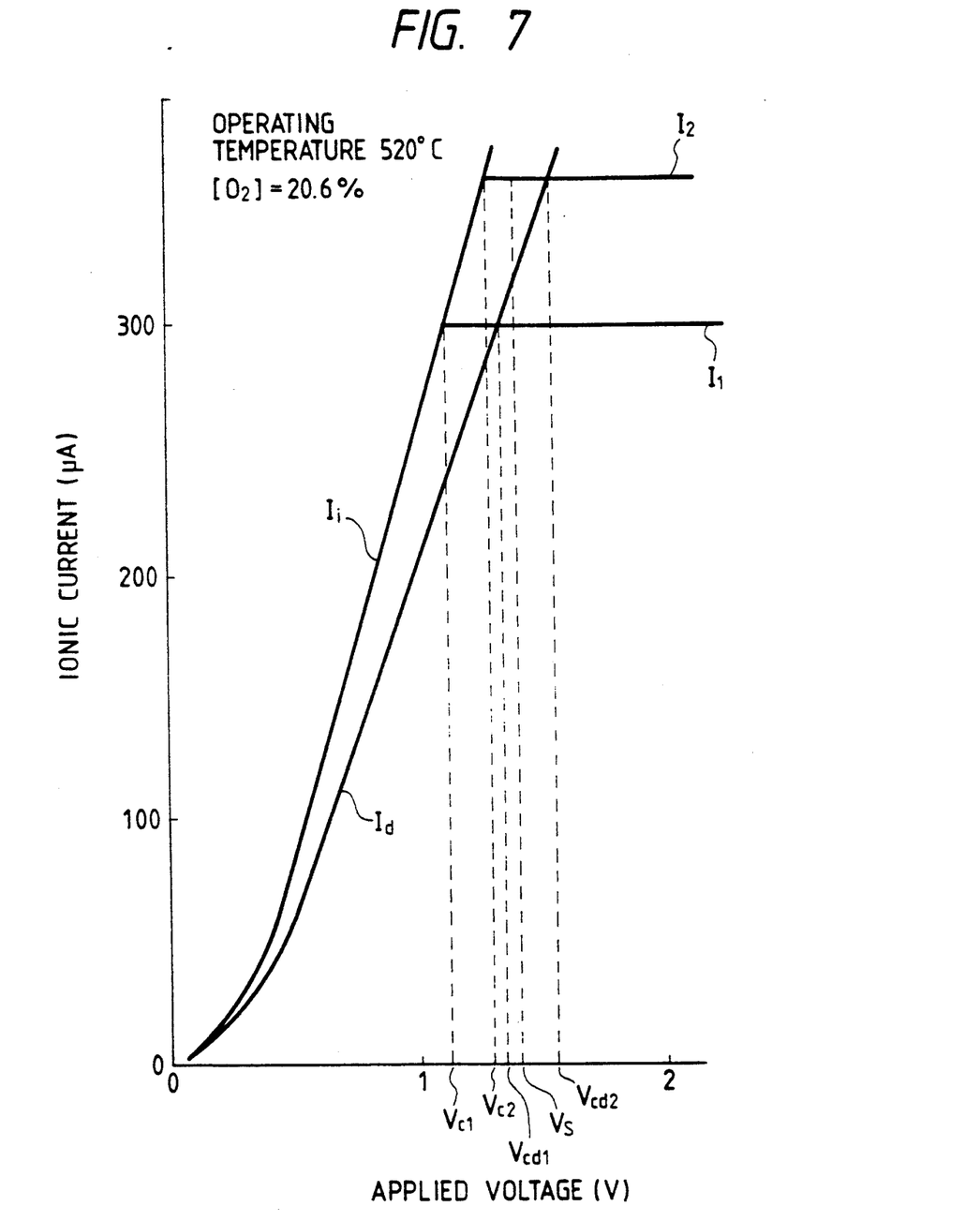
FIG. 7 shows ionic current-applied voltage characteristics.

FIG. 7 shows typical V-I characteristics of the first and second sensor elements having limiting currents different from each other. The operating temperature is 520° C. and the oxygen concentration is about 20.6%. Measurement voltage applied to the positive electrodes 21a and 22a and the negative electrodes 21b and 22b is about 1.4 V. The negative electrodes 21b and 22b each have substantially the same area as the positive electrodes 21a and 22a. A solid thin line $I_i$ shows initial V-I characteristics of the first and second sensor elements, in a high concentration region of 20.6% or more in oxygen concentration. Even though the solid-electrolyte plate 1 having the positive electrodes 21a and 22a and negative electrodes 21b and 22b can transport a large quantity of oxygen ions at an applied voltage of 1.4 V, the quantity of oxygen molecules that diffuse from the external space into the closed spaces 61 and 62 is very small. As a result, limiting currents $I_1$ and $I_2$ shown in FIG. 7 by thick solid lines $I_1$ and $I_2$ cab be measured. The limiting currents $I_1$ and $I_2$ depend on the diffusion resistance $R_{d1}$ and $R_{d2}$ at the windows 41 and 42, respectively.

An ion conducting region is defined as a region in which ionic currents rely on applied voltages. A limiting current region is defined as a region in which ionic currents do not rely on applied voltages and a constant current value is retained. A transition voltage $V_c$ is defined as a voltage at which transition occurs from the ion conducting region to the limiting current region. The transition voltage $V_c$ becomes higher with an increase in the limiting current. Transition voltage $V_{c1}$ of the first sensor element is lower than transition voltage $V_{c2}$ of the second sensor element. On the other hand, once the negative electrodes 21b and 22b have been deteriorated because of adhesion of dust or the like such as fine oxide, the solid-electrolyte plate 1 having the positive electrodes 21a and 22a and negative electrodes 21b and 22b can no longer transport oxygen ions in so larger a quantity than the initial transport quantity that the V-I characteristics change from the initial characteristics $I_i$ to the deteriorated characteristics $I_d$ shown by a thin solid line $I_d$. As a result, the transition voltages $V_{c1}$ and $V_{c2}$ increases to $V_{cd1}$ and $V_{cd2}$, respectively.

Since the measurement voltage $V_s$ is set at a higher voltage than the $V_{c2}$ at the initial stage, the mutual relations between $V_s$, $V_{cd1}$ and $V_{cd2}$ necessarily change in the following order, with progress of the deterioration of the negative electrodes 21b and 22b. That is to say, $V_s > V_{cd2}(=V_{c2}) > V_{cd1}(=V_{c2})$ at the initial stage, $V_{cd2} > V_s > V_{cd1}$ at the intermediate stage, and $V_{cd2} > V_{cd1} > V_s$ at the final stage. Once the transition voltage $V_{c2}$ has become higher than the measurement voltage $V_s(=1.4 V)$ for the first time in the intermediate deterioration, the second sensor element can no longer retain the limiting current $I_2$. On the other hand, since $V_s$ is higher than $V_{cd1}$ on that occasion, the first sensor element retains the limiting current $I_1$. From these facts, it is seen that the mutual relation between $I_1$ and $I_2$ changes when $V_{cd2}$ becomes higher than $V_s$. It is clear that the deterioration of the negative electrodes 21b and 22b that may lead to $V_{cd2} > V_s$ can be detected based on the logic as previously set forth with regard to the detection of dust or the like and fine cracks.

Figure 8:
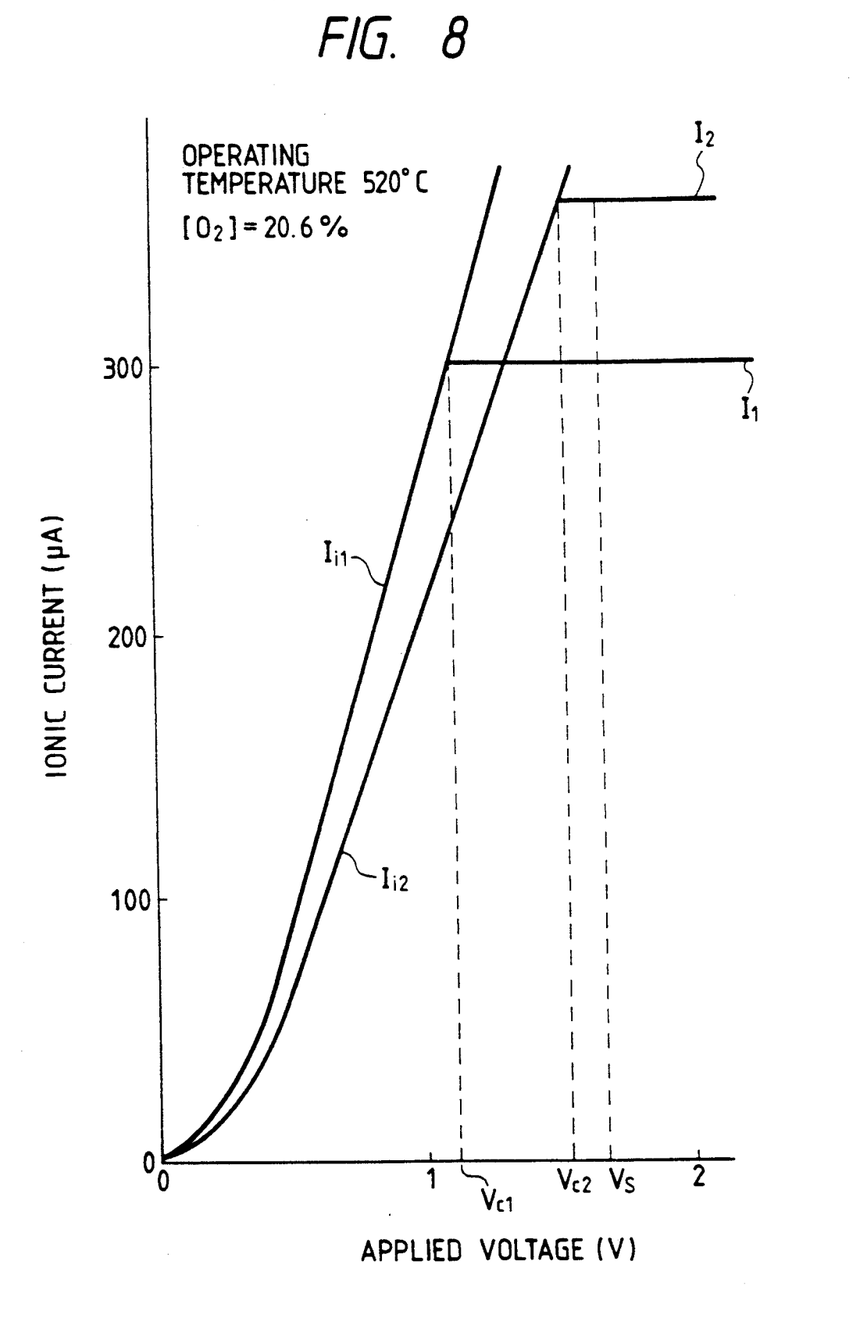
FIG. 8 shows other ionic current-applied voltage characteristics.

In the case when the negative electrode 21b has a large area than the negative electrodes 22b, the deterioration can be detected based on the same logic. FIG. 8 shows typical initial V-I characteristics of the first and second sensor elements. Thin solid lines $I_{i1}$ and $I_{i2}$ indicate typical initial V-I characteristics of the first and second sensor elements in a high concentration region of 20.6% or more in oxygen concentration. Since the negative electrode 21b has a larger area than the negative electrode 22b, $I_{l1}$ is always larger than $I_{l2}$. Thick solid lines $I_1$ and $I_2$ indicate limiting currents of the first and second sensor elements, respectively. Measurement voltage $V_s$ is so set to give $V_s > V_{c2}$. Since $V_{c1}$ is lower than $V_{c2}$, it is apparent that the deterioration of the negative electrode 22b can be detected based on the same logic as set forth in relation to FIG. 7.

In order to detect the deterioration of the negative electrode 21b or 22b, it is important for the transition voltages $V_{c1}$ and $V_{c2}$ to be different from each other and for the measurement voltage $V_s$ to be greater than the greatest transition voltage among $V_{c1}$ and $V_{c2}$.

Figure 9:
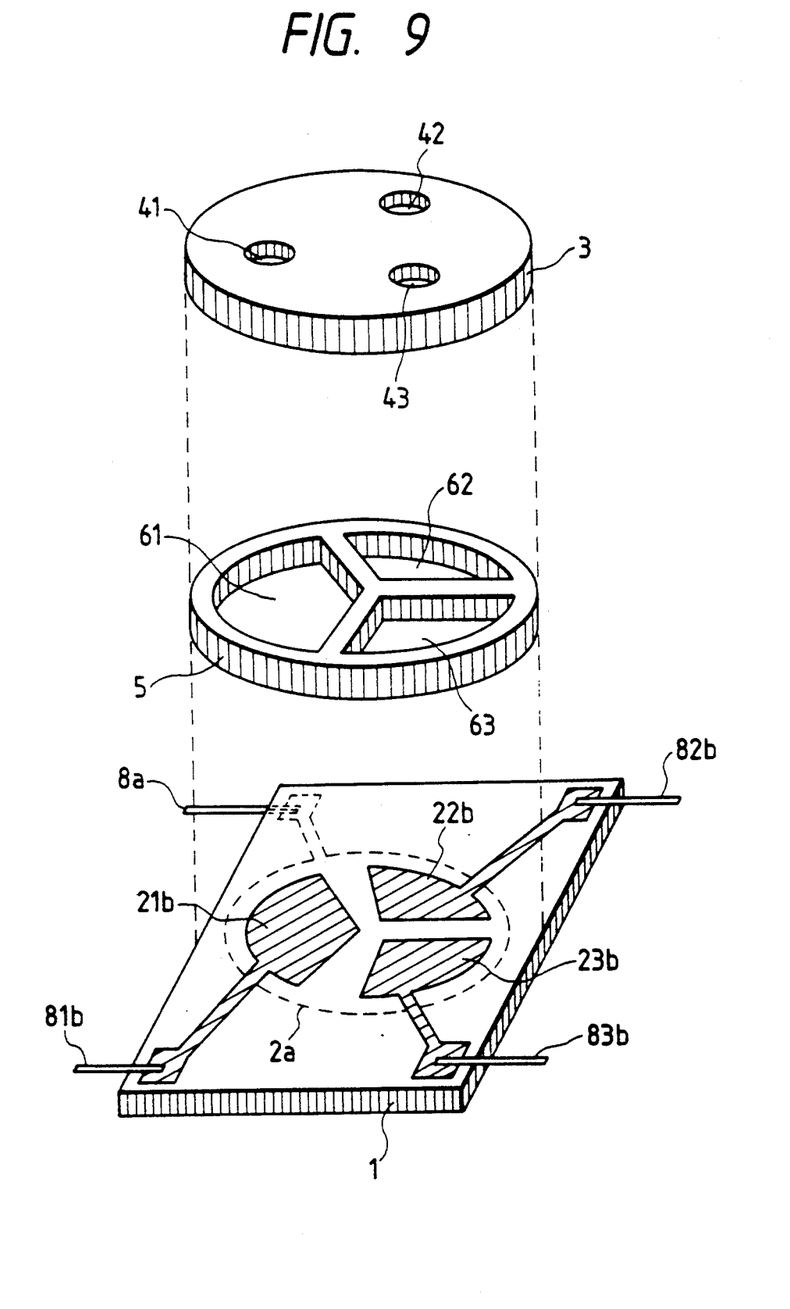
FIGS. 9 and 10 are each a perspective exploded view of an oxygen sensor according to still another embodiment of the present invention.
Figure 10:
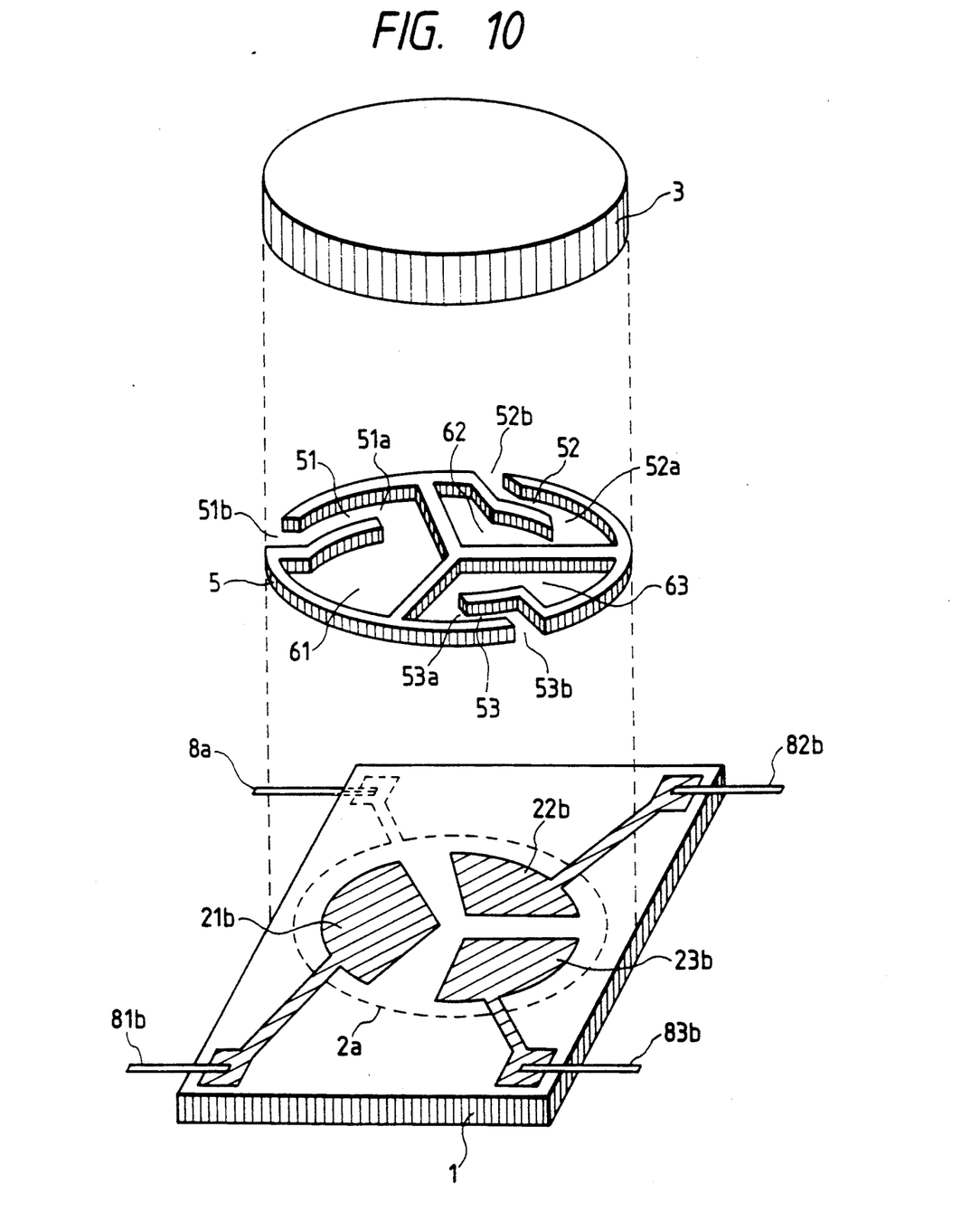

It is apparent that the positive electrodes 21a and 22a may instead be comprised of a single electrode, and the negative electrodes 21b and 22b may be separately formed or inversely need not be separated. In FIGS. 4 and 6, examples have been given in which a plurality of DC power sources $E_1$ and $E_2$ are used. If the resistances $R_1$ and $R_2$ are small, the voltage drop (signal voltages) at both ends of these resistances can be made sufficiently smaller than that of $E_1$ and $E_2$. Hence, it would be apparent that a single DC power source may be used. In addition, although the invention has been herein described by giving the sensor structure that two sensor elements are integrated on one solid-electrolyte plate 1, it is more preferable that a greater plurality of sensor elements are integrated as shown in FIGS. 9 and 10. The reason therefor is that more mutual relations between a greater plurality of limiting currents can be utilized.

What is claimed is:

1. An oxygen sensor comprising:
an oxygen ion conductive solid-electrolyte plate having first and second opposite surfaces;
a plurality of negative electrodes formed on the first surface of said solid-electrolyte plate;
a plurality of positive electrodes formed on the second surface of said solid-electrolyte plate, at the positions respectively opposed to said plurality of negative electrodes;
a spacer hermetically secured to the first surface of said electrolyte plate and disposed in such a way that it surrounds each of the plurality of negative electrodes;
a sealing plate hermetically secured to said spacer;
a plurality of closed spaces being defined by said first surface of the solid-electrolyte plate, said spacer and said sealing plate; and said closed spaces being formed in such a way that each of said plurality of closed spaces contains one of the plurality of negative electrodes; and
a plurality of windows so provided that oxygen molecules present in the external space may diffuse into each of said plurality of closed spaces, each of a respective said positive electrode, negative electrode, window and closed space forming a sensor element, whereby detection of limiting currents passing through a plurality of said sensor elements facilitates detection of deterioration in said oxygen sensor; wherein said plurality of windows are comprised of a plurality of small orifices formed in said solid-electrolyte plate, and each of the plurality of small orifices communicates with each of the plurality of closed spaces.

2. An oxygen concentration detecting apparatus comprising:
an oxygen ion conductive solid-electrolyte plate having first and second opposite surface;
a plurality of negative electrodes formed on the first surface of said solid-electrolyte plate;
a plurality of positive electrodes formed on the second surface of said solid-electrolyte plate, at the positions respectively opposed to said plurality of negative electrodes;
a spacer hermetically secured to the first surface of said electrolyte plate and disposed in such a way that it surrounds each of the plurality of negative electrodes;
a sealing plate hermetically secured to said spacer; a plurality of closed spaces being defined by said first surface of the solid-electrolyte plate, said spacer and said sealing plate; and said closed spaces being formed in such a way that each of said plurality of closed spaces contains one of the plurality of negative electrodes;
a plurality of windows so provided that oxygen molecules present in the external space may diffuse into each of said plurality of closed spaces, said plurality of windows are comprised of a plurality of small orifices formed in said solid-electrolyte plate, and each of the plurality of small orifices communicates with each of the plurality of closed spaces; and
a plurality of detecting means for detecting oxygen ionic currents that pass through a plurality of electrode pairs comprised of said plurality of negative electrodes and said plurality of positive electrodes, in order to detect a deterioration;
said detecting means comprising;
a plurality of DC power sources;
a plurality of resistance means; each of said plurality of DC power sources and each of said plurality of resistance means being connected in series to each of said plurality of negative electrodes and said plurality of positive electrodes, and voltages at both ends of each of said plurality of resistance means being signal voltages corresponding with oxygen concentrations;
a voltage ratio detecting means for detecting the ratio of two signal voltages different from each other among a plurality of signal voltages; and
a comparison means for comparing said signal voltage ratio with a given value.

3. An oxygen concentration detecting apparatus according to claim 2, wherein a plurality of resistances are each determined in such a way that all of the plurality of signal voltages have the same given value.

4. An oxygen concentration detecting apparatus according to claim 2, wherein said detecting means is provided with a total-voltage detecting means for detecting part or all of the plurality of signal voltages.

* * * * *